(12) United States Patent
Zhou et al.

(10) Patent No.: US 9,174,032 B2
(45) Date of Patent: Nov. 3, 2015

(54) SUBINTIMAL REENTRY SYSTEM

(71) Applicant: Boston Scientifc Scimed, Inc., Maple Grove, MN (US)

(72) Inventors: Pu Zhou, Maple Grove, MN (US); Huisun Wang, Maple Grove, MN (US); Daniel Quillin, Eden Prairie, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 180 days.

(21) Appl. No.: 13/940,827

(22) Filed: Jul. 12, 2013

(65) Prior Publication Data

US 2014/0018837 A1 Jan. 16, 2014

Related U.S. Application Data

(60) Provisional application No. 61/671,398, filed on Jul. 13, 2012.

(51) Int. Cl.
*A61M 29/00* (2006.01)
*A61M 25/10* (2013.01)
*A61M 25/09* (2006.01)
(Continued)

(52) U.S. Cl.
CPC ......... *A61M 25/104* (2013.01); *A61M 25/0155* (2013.01); *A61M 25/0194* (2013.01); *A61M 25/09* (2013.01); *A61M 25/0108* (2013.01); *A61M 2025/0095* (2013.01); *A61M 2025/0183* (2013.01); *A61M 2025/0197* (2013.01); *A61M 2025/0681* (2013.01)

(58) Field of Classification Search
CPC ................ A61M 29/00; A61M 29/02; A61M 2025/0197; A61M 2025/0095; A61M 2025/0096; A61M 25/0194; A61M 25/0155; A61B 2017/22044; A61B 2017/22048; A61B 2017/22071; A61B 2017/22095
USPC .................. 606/194, 185, 167, 159, 190–192; 600/585, 424, 146, 434; 604/509, 272, 604/96.01, 99.01, 101.01
See application file for complete search history.

(56) References Cited

U.S. PATENT DOCUMENTS 5,830,222 A 11/1998 Makower
5,935,108 A 8/1999 Katoh et al.
(Continued)

FOREIGN PATENT DOCUMENTS

| GB | 2469073 | * | 6/2010 | ............ A61M 25/10 |
| WO | 2008063621 A2 | | 5/2008 | |
| WO | 2013036419 A1 | | 3/2013 | |

*Primary Examiner* — Todd Manahan
*Assistant Examiner* — Majid Jamialahmadi
(74) *Attorney, Agent, or Firm* — Seager, Tufte & Wickhem LLP

(57) ABSTRACT

A subintimal recanalization catheter system for recanalizing a blood vessel. The system includes a support catheter and a balloon catheter configured to extend through the support catheter. The support catheter includes a tubular portion and an extension segment extending distal of the distal opening of the tubular portion. The balloon catheter, having a balloon secured to a distal portion thereof, is positionable through the tubular portion of the support catheter to position the balloon alongside the extension segment. The system is configured to be advanced into a subintimal space between a first tissue layer and a second tissue layer of a blood vessel wall where the balloon may be inflated against the extension segment to cause a distal portion of the catheter shaft of the balloon catheter to deflect toward the vessel lumen within the subintimal space to facilitate reentry into the vessel lumen.

13 Claims, 12 Drawing Sheets

(51) Int. Cl.
   *A61M 25/01*    (2006.01)
   *A61M 25/00*    (2006.01)
   *A61M 25/06*    (2006.01)

(56) References Cited

U.S. PATENT DOCUMENTS

| | | | |
|---|---|---|---|
| 5,938,671 | A | 8/1999 | Katoh et al. |
| 5,968,064 | A | 10/1999 | Selmon et al. |
| 6,010,449 | A | 1/2000 | Selmon et al. |
| 6,068,638 | A | 5/2000 | Makower |
| 6,120,516 | A | 9/2000 | Selmon et al. |
| 6,159,225 | A | 12/2000 | Makower |
| 6,190,353 | B1 | 2/2001 | Makower et al. |
| 6,217,527 | B1 | 4/2001 | Selmon et al. |
| 6,217,549 | B1 | 4/2001 | Selmon et al. |
| 6,221,049 | B1 | 4/2001 | Selmon et al. |
| 6,231,546 | B1 | 5/2001 | Milo et al. |
| 6,231,587 | B1 | 5/2001 | Makower |
| 6,235,000 | B1 | 5/2001 | Milo et al. |
| 6,241,667 | B1 | 6/2001 | Vetter et al. |
| 6,398,798 | B2 | 6/2002 | Selmon et al. |
| 6,506,178 | B1 | 1/2003 | Schubart et al. |
| 6,508,825 | B1 | 1/2003 | Selmon et al. |
| 6,511,458 | B2 | 1/2003 | Milo et al. |
| 6,514,217 | B1 | 2/2003 | Selmon et al. |
| 6,579,302 | B2 | 6/2003 | Duerig et al. |
| 6,599,304 | B1 | 7/2003 | Selmon et al. |
| 6,638,247 | B1 | 10/2003 | Selmon et al. |
| 6,663,577 | B2 | 12/2003 | Jen et al. |
| 6,719,725 | B2 | 4/2004 | Milo et al. |
| 6,955,175 | B2 | 10/2005 | Stevens et al. |
| 7,004,173 | B2 | 2/2006 | Sparks et al. |
| 7,179,270 | B2 | 2/2007 | Makower |
| 7,229,421 | B2 | 6/2007 | Jen et al. |
| 7,357,794 | B2 | 4/2008 | Makower et al. |
| 7,740,623 | B2 | 6/2010 | Nayak et al. |
| 7,918,859 | B2 | 4/2011 | Katoh et al. |
| 7,918,870 | B2 | 4/2011 | Kugler et al. |
| 7,938,819 | B2 | 5/2011 | Kugler et al. |
| 8,025,655 | B2 | 9/2011 | Kugler et al. |
| 8,083,727 | B2 | 12/2011 | Kugler et al. |
| 2001/0000041 | A1 | 3/2001 | Selmon et al. |
| 2001/0012924 | A1 | 8/2001 | Milo et al. |
| 2002/0103459 | A1 | 8/2002 | Sparks et al. |
| 2002/0128677 | A1 | 9/2002 | Duerig et al. |
| 2003/0120195 | A1 | 6/2003 | Milo et al. |
| 2003/0139763 | A1 | 7/2003 | Duerig et al. |
| 2004/0167554 | A1 | 8/2004 | Simpson et al. |
| 2004/0230219 | A1 | 11/2004 | Roucher, Jr. |
| 2005/0171478 | A1 | 8/2005 | Selmon et al. |
| 2006/0094930 | A1 | 5/2006 | Sparks et al. |
| 2006/0184011 | A1 | 8/2006 | Macaulay et al. |
| 2006/0276749 | A1 | 12/2006 | Selmon et al. |
| 2007/0093779 | A1 | 4/2007 | Kugler et al. |
| 2007/0093780 | A1 | 4/2007 | Kugler et al. |
| 2007/0093781 | A1 | 4/2007 | Kugler et al. |
| 2007/0093782 | A1 | 4/2007 | Kugler et al. |
| 2007/0208368 | A1 | 9/2007 | Katoh et al. |
| 2007/0265596 | A1 | 11/2007 | Jen et al. |
| 2008/0033423 | A1 | 2/2008 | Peacock |
| 2008/0125748 | A1 | 5/2008 | Patel |
| 2008/0154172 | A1 | 6/2008 | Mauch |
| 2008/0200896 | A1 | 8/2008 | Shmulewitz et al. |
| 2008/0228171 | A1 | 9/2008 | Kugler et al. |
| 2008/0243065 | A1 | 10/2008 | Rottenberg et al. |
| 2008/0243067 | A1 | 10/2008 | Rottenberg et al. |
| 2008/0249397 | A1 | 10/2008 | Kapadia |
| 2009/0005755 | A1 | 1/2009 | Keith et al. |
| 2009/0088685 | A1 | 4/2009 | Kugler et al. |
| 2009/0093791 | A1 | 4/2009 | Heuser |
| 2009/0124899 | A1 | 5/2009 | Jacobs et al. |
| 2009/0209910 | A1 | 8/2009 | Kugler et al. |
| 2009/0254107 | A1 | 10/2009 | Katoh et al. |
| 2009/0264826 | A1 | 10/2009 | Thompson |
| 2009/0292296 | A1 | 11/2009 | Pansky et al. |
| 2009/0299171 | A1 | 12/2009 | Duffy et al. |
| 2009/0299402 | A1 | 12/2009 | Orihashi et al. |
| 2010/0063534 | A1 | 3/2010 | Kugler et al. |
| 2010/0069945 | A1 | 3/2010 | Olson et al. |
| 2010/0125244 | A1 | 5/2010 | McAndrew |
| 2010/0317973 | A1 | 12/2010 | Nita |
| 2011/0112564 | A1 | 5/2011 | Wolf |
| 2011/0144677 | A1 | 6/2011 | Ward et al. |
| 2011/0166591 | A1 | 7/2011 | Katoh et al. |
| 2013/0072957 | A1* | 3/2013 | Anderson .................. 606/194 |
| 2014/0194776 | A1* | 7/2014 | Gunday et al. .............. 600/567 |
| 2014/0228876 | A1* | 8/2014 | Copeta et al. .............. 606/194 |

* cited by examiner

SUBINTIMAL REENTRY SYSTEM

CROSS-REFERENCE TO RELATED APPLICATION

This application claims the benefit of U.S. Provisional Application Ser. No. 61/671,398, filed Jul. 13, 2012, the entire disclosure of which is incorporated herein by reference.

TECHNICAL FIELD

This disclosure relates to systems and methods for recanalization of an occluded blood vessel. More particularly, the disclosure is directed to systems and methods for reentry of a catheter system from the subintimal space into the true lumen of the blood vessel.

BACKGROUND

A chronic total occlusion (CTO) is an arterial vessel blockage that obstructs blood flow through a vessel. A CTO generally results from a diseased condition called arthrosclerosis, which can occur in both coronary and peripheral arteries. In some instances, it may be difficult or impossible to penetrate the CTO with a medical device in an antegrade direction to recanalize the vessel. Accordingly, techniques have been developed for creating a subintimal pathway (a path between the intimal and adventitial tissue layers of the vessel wall) around the occlusion and then reentering the true lumen of the vessel distal of the occlusion. In some instances, reentering the true lumen from the subintimal space and/or recanalization pathway may be difficult. For example, some methods for subintimal reentry rely on the difference between the stiffness of the outer adventitial layer and the inner intimal layer of a vessel wall to facilitate reentry into the vessel lumen. Generally, the outer adventitial layer is stiffer than the inner intimal layer. This difference in stiffness allows the intimal layer to yield first if a medical device applies an outwardly directed pressure from between the two tissue layers, thus deflecting the distal portion of the catheter shaft toward the vessel lumen. However, in some instances calcification (accumulation of plaque) on the inner surface of the vessel wall may increase the stiffness of the intimal layer, reducing the difference in stiffness of the tissue layers, and thereby making it difficult for catheters to reenter the vessel lumen. In such instances, the risk of inadvertent perforation or dissection of the vessel wall, or tamponade (blood leakage out of an artery around the heart or peripheral organs) may increase during a subintimal recanalization procedure. Accordingly, it is desirable to provide alternative recanalization systems and/or methods having improved reentry mechanisms for recanalization of a blood vessel in which a CTO is present.

SUMMARY

The disclosure is directed to several alternative designs and methods of using medical device structures and assemblies, and uses thereof.

Accordingly, one illustrative embodiment is a subintimal recanalization catheter system for recanalizing a blood vessel having an occlusion in a lumen therein. The catheter system includes an elongate shaft. The elongate shaft further includes a tubular portion having a lumen extending through it to a distal opening. In addition, an extension segment extends distal of the distal opening. Furthermore, the system includes a balloon catheter having a balloon secured to a distal portion of a catheter shaft. The balloon catheter may extend through the lumen of the elongate shaft to position the balloon of the balloon catheter distal of the distal opening. The catheter system may be configured to be advanced into a subintimal space between a first tissue layer and a second tissue layer of a wall of the blood vessel. The balloon may be configured to be inflated against the extension segment to cause a distal portion of the catheter shaft to deflect toward the lumen of the blood vessel within the subintimal space to facilitate reentry into the lumen of the blood vessel.

Another illustrative embodiment is a subintimal recanalization catheter system for recanalizing a blood vessel having an occlusion therein. The catheter system includes a support catheter including an elongate shaft. The elongate shaft includes a tubular portion having a lumen extending through it to a distal opening. In addition, an extension segment may extend distal of the distal opening. The system further includes a balloon catheter having a balloon secured to a distal portion of a catheter shaft. The balloon catheter may extend through the lumen of the elongate shaft to position the balloon of the balloon catheter alongside the extension segment distal of the distal opening. The catheter system may be configured to be advanced into a subintimal space between a first tissue layer and a second tissue layer of a wall of the blood vessel. The balloon may be configured to be inflated between the extension segment and the first tissue layer.

Yet another illustrative embodiment is a method of recanalizing a blood vessel having an occlusion in a lumen therein. The method includes advancing a support catheter into a subintimal space between a first tissue layer and a second tissue layer of a wall of a blood vessel. The support catheter includes an elongate shaft including a tubular portion having a lumen extending through it to a distal opening. In addition, an extension segment may extend distal of the distal opening. The method further includes positioning a balloon of a balloon catheter beside the extension segment within the subintimal space between the first tissue layer and the second tissue layer. The balloon is then inflated between the extension segment and the first tissue layer such that the balloon is inflated against the extension segment. Inflating the balloon against the extension segment may cause a distal portion of the catheter shaft to deflect toward the lumen of the blood vessel within the subintimal space to facilitate reentry into the lumen of the blood vessel.

The above summary of some example embodiments is not intended to describe each disclosed embodiment or every implementation of the present disclosure.

BRIEF DESCRIPTION OF THE DRAWINGS

The invention may be more completely understood in consideration of the following detailed description of various embodiments in connection with the accompanying drawings, in which:

FIG. 1A is a side view, FIG. 1B is a top view, and FIG. 1C is a cross-sectional view of the catheter taken along plane 1C-1C' of FIG. 1A;

FIG. 3A is a side view, FIG. 3B is a top view, and FIG. 3C is a cross-sectional view of the catheter taken along plane 3C-3C' of FIG. 3A;

Figure 1A:
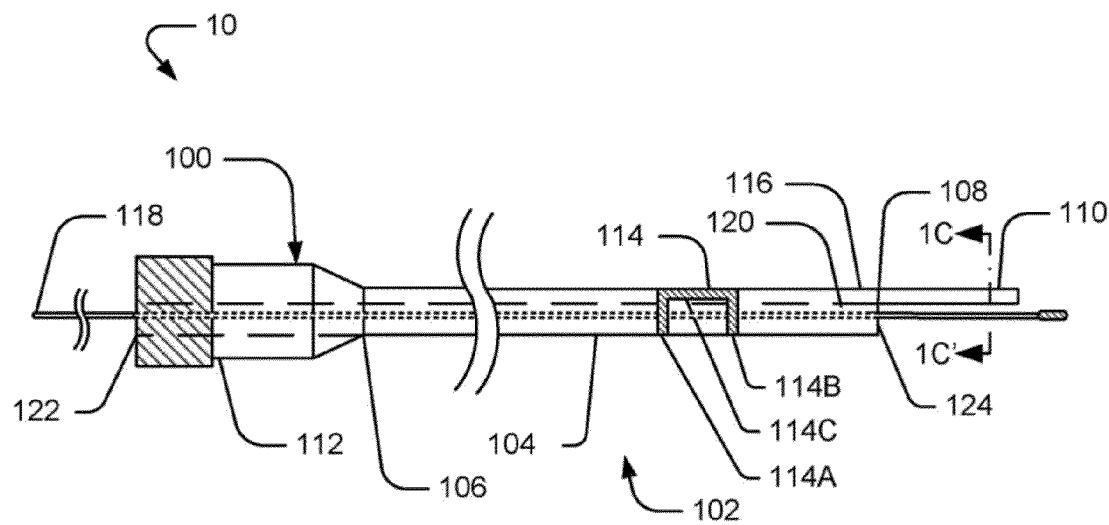
FIGS. 1A-1C illustrate an exemplary support catheter, where

While the invention of the present disclosure is amenable to various modifications and alternative forms, specifics thereof have been illustrated by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is provided in the claims or elsewhere in this specification. All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features, and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

While the devices and methods described herein are discussed relative to recanalization of blood vessels blocked by a CTO, it is contemplated that the devices and methods may be used in other applications, where recanalization of a blood vessel is desired.

The present disclosure provides methods and systems to reenter the true lumen of a blood vessel during recanalization of the blood vessel. To this end, the methods and systems may employ a catheter system having one or more of a support catheter, a balloon catheter, a penetration member disposed within the balloon catheter, and/or a guidewire disposed within the support catheter.

An exemplary subintimal recanalization catheter system 10 is set out in the present disclosure. Components of recanalization catheter system 10 include a support catheter 100, shown in FIGS. 1A-1C, and a balloon catheter 200, shown in FIG. 2. Support catheter 100 may include a generally elongated shaft 102, having a distal portion 108 including an extension segment 110 having a cross-sectional area smaller than that of the remainder of the support catheter 100. Guidewire 118 may be slidably disposed within a lumen of support catheter 100. Balloon catheter 200 may include an expandable member, shown here as balloon 214, mounted on a distal portion thereof. Penetration member 224 may be extendable distally from the end of the balloon catheter 200, which in some instances may include a sharpened tip.

Figure 1B:
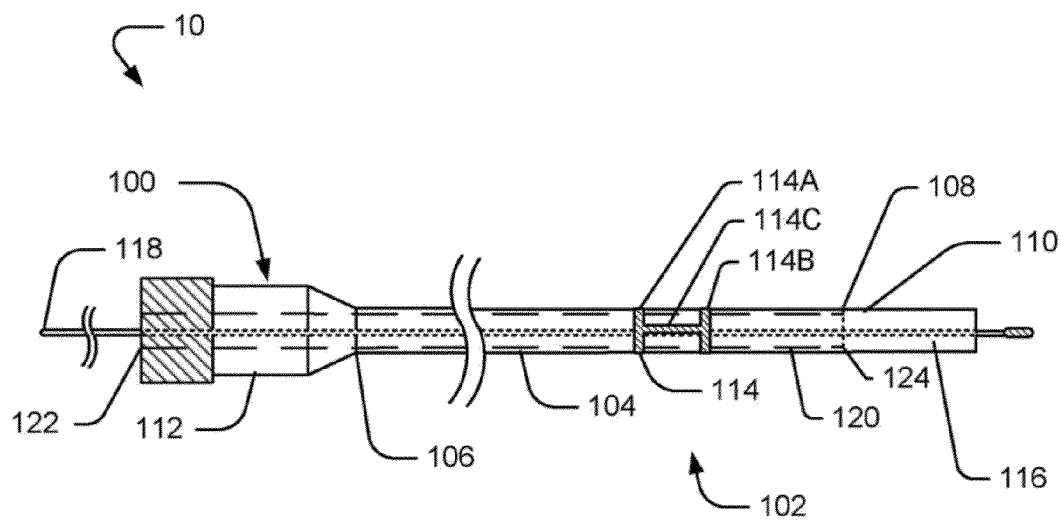
Figure 1C:
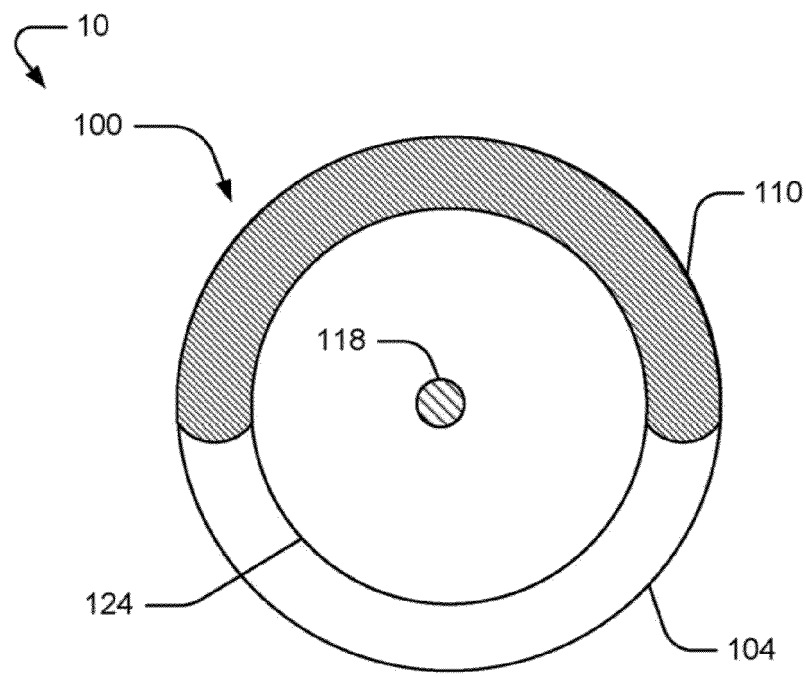

FIGS. 1A and 1B are side and top views, respectively, and FIG. 1C is a cross-sectional view, taken along plane 1C-1C' of FIG. 1A. Support catheter 100 may include an elongate shaft 102, which may include a tubular portion 104 extending from a proximal end 106 to a distal end 108, as well as an extension segment 110 extending distally beyond the distal end 108 of the tubular portion 104. A hub assembly 112, configured to assist an operator to manipulate the support catheter 100, may be attached to the proximal end 106, and a marker band 114 may be embedded in, positioned on, or otherwise provided with the tubular portion 104 proximate to the distal end 108.

Support catheter 100 may include one or more internal lumens, such as a lumen shown in FIGS. 1A-1B, namely, catheter lumen 120. The catheter lumen 120 may be configured to receive the balloon catheter 200 (FIG. 2) and/or the guidewire 118 therethrough and may extend from the hub assembly 112 to the distal end 108 of the tubular portion 104, in some instances. The catheter lumen 120 may communicate with one or more ports or openings in support catheter 100. For example, the proximal end of catheter lumen 120 may terminate at port 122 and its distal end may terminate at a distal opening 124 located at, or near, the distal end 108 of the tubular portion 104.

The support catheter 100 may be configured to be advanced over the guidewire 118 for delivery to a remote location in the vasculature of a patient. In some embodiments, the support catheter 100 may be configured as a single operator exchange (SOE) (monorail or rapid exchange) catheter, having a rapid exchange port (not shown) located distal of the proximal end 106 of the tubular portion 104 for inserting the guidewire 118 into the catheter lumen 120. In other embodiments, as shown, the support catheter 100 may be configured as an over the wire (OTW) catheter, where the guidewire 118 may be inserted into the catheter lumen 120 through port 122. Furthermore, the guidewire 118 may be extended distally from the support catheter 100 through distal opening 124. It is noted that other catheter constructions are contemplated.

In some embodiments, the tubular portion 104 may be configured with a substantially circular cross-section extending between the proximal and distal ends 106, 108. Other suitable cross-sectional shapes may be elliptical, oval, polygonal, or irregular. In addition, the tubular portion 104 may be flexible along its entire length or adapted for sufficient flexure to navigate through turns in body lumens. Rigidity may provide the necessary force to urge the tubular portion 104 forward. The cross-sectional dimensions and/or length of the tubular portion 104 may vary according to the desired application to provide access to a desired location in the vasculature. In some instances, a 6F or a 5F catheter may be employed, where 'F', also known as French catheter scale, is a unit to measure catheter diameter (1F=⅓ mm). In addition, the tubular portion 104 or a portion thereof may be selectively steerable. Mechanisms such as, pull wires or other actuators may be used to selectively steer the tubular portion 104.

FIG. 1C illustrates a cross-section of support catheter 100 across plane 1C-1C'. Here, extension segment 110, and the guidewire 118 are shown in cross-section, extending distally from tubular portion 104 beyond the distal opening 124. It can be seen that extension segment 110 may continue the upper portion of the profile of tubular portion 104 in the form of a closed semi-annulus.

In the illustrated embodiment, the extension segment 110 may extend distally beyond the distal end 108. In some embodiments, as illustrated in FIGS. 1A-1C, the extension segment 110 may be a semi-circular extension of the upper half of tubular portion 104. Other cross-sectional shapes of the extension segment 110 may be semi-elliptical, semi-oval, polygonal, or irregular. In general, the extension segment 110 may have any cross-sectional shape that may provide a suitable surface against which the balloon 214 of the balloon catheter 200 may be inflated against. For example, the extension segment 110 may have a concave surface such that the concave surface may face the balloon 214 of the balloon catheter 200 upon extending the balloon 214 of the balloon catheter 200 distally through distal opening 124, as is described in detail below. The stiffness (rigidity or flexibility) of the extension segment 110 may depend upon its intended use as discussed further herein. In general, the extension segment 110 may be designed with stiffness greater than the stiffness of the intimal layer of the vessel wall where the subintimal reentry is desired. Similarly, the length and thickness of the extension segment 110 may be sized appropriately to accommodate the thickness of the vessel wall.

The extension segment 110 may be integrally formed with, fixedly secured to, or otherwise coupled to tubular portion 104. Coupling or securement may be accomplished by methods or mechanisms such as welding, molding, thermal bonding, adhesive bonding, snap fit or similar techniques.

The tubular portion 104 and the extension segment 110 may be formed from any suitable biocompatible material, such as suitable polymers or metals. Both elements may be formed from the same material, or different materials may be employed for their various characteristics. In general, suitable polymeric materials may include, for example, polyamide, PEBAX® (polyether block amide), polyurethane, polyethylene, nylon, and polyethylene terepthalate. Metallic materials, such as stainless steel or nitinol may also be used, if desired. Alternatively, a combination of polymeric and metallic materials may be employed as well. A suitable combination material may be a polymeric material reinforced with metallic wires, a braid and/or a coil to increase rigidity of a portion of the elongate shaft 102. Furthermore, the elongate shaft 102, or a portion thereof, may be coated with a suitable low-friction material, such as polytetrafluoroethylene (PTFE), such as TEFLON®, polyetheretherketone (PEEK), polyimide, nylon, polyethylene, hydrophilic coatings or other lubricious polymer coatings to reduce friction.

The marker band 114, located at a distal portion of the elongate shaft 102, may be formed of radiopaque material in a distinctive pattern to facilitate locating the precise position and rotational orientation of elongate shaft 102 within the vessel wall using appropriate imaging techniques during a medical procedure. As noted above, this indicia may be located proximate to the distal end 108 on the tubular portion 104. In some embodiments, as illustrated in FIGS. 1A-1B, the distinctive pattern may include circumferential rings 114A and 114B connected by a longitudinally oriented bar 114C. Bar 114C may align with the central axis of the extension segment 110 allowing the operator to determine the rotational orientation of the extension segment 110 within the blood vessel.

The marker band 114 may be formed of a metal construct, such as tungsten, platinum or a platinum-chromium alloy, molybdenum or a molybdenum alloy, or a polymer having a radiopaque filler dispersed therein. For example, marker band 114 may be made of a suitable biocompatible polymeric material, which may be impregnated with, or otherwise include, one or more radiopaque materials, such as metal, metal flakes, metal powder, ceramics, ceramics powder, barium sulfate ($BaSO_4$), bismuth subcarbonate ($Bi_2O_2(CO_3)$), bismuth trioxide ($Bi_2O_3$), or any other suitable radiopaque material. The marker band 114 may be secured to the tubular portion 104 utilizing a variety of methods including adhesive bonding, crimping, thermal bonding, or any other suitable means.

Guidewire 118, as is known in the art, may be advanced through the patient's vasculature to the selected treatment site to provide a pathway over which support catheter 100 may subsequently be advanced to the treatment site. The guidewire 118 may be a metallic or polymeric wire, formed of stainless steel or nitinol, for example. The dimensions of guidewire 118 may depend on the therapeutic application at hand. The length of the guidewire 118 may depend on the length of the support catheter 100, the target location in the anatomy, and the extent to which the guidewire 118 may need to extend distally beyond the support catheter 100. In some embodiments, the guidewire 118 may have a diameter ranging between 0.014 inches and 0.035 inches, for example.

Catheter lumen 120 may be configured to carry the guidewire 118 and/or the balloon catheter 200 (FIG. 2), respectively. The catheter lumen 120 may have a diameter sized to accommodate the guidewire 118 and/or the balloon catheter 200. For example, in some embodiments, the diameter of the catheter lumen 120 may be about 0.05 inches to about 0.10 inches.

Figure 2:
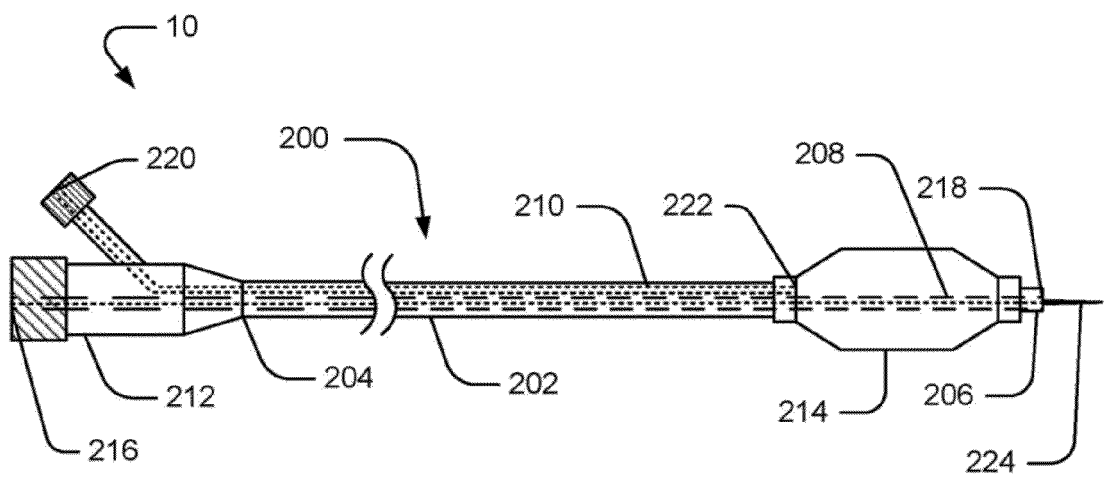
FIG. 2 illustrates an exemplary balloon catheter.

FIG. 2 is a side view of an exemplary balloon catheter 200. As shown, a catheter shaft 202 may extend between a proximal end 204 and a distal end 206, with a guidewire lumen 208 and an inflation lumen 210 extending between the ends 204, 206. A hub assembly 212 may be attached to the proximal end 204, and a balloon 214 may be mounted on the catheter shaft 202 proximate to the distal end 206. The guidewire lumen 208 may terminate at a port 216 at the hub assembly 212 and a distal opening 218 at the distal end 206. The inflation lumen 210 may communicate with a port 220 at the hub assembly 212 and a port 222, and may be in fluid communication with the balloon 214. In some instances, a penetration member 224 may be slidably disposed within the guidewire lumen 208, configured to advance out of the distal opening 218.

The catheter shaft 202 may be an elongate sheath or a tubular member configured to fit within the catheter lumen 120 (FIGS. 1A-1C) of the support catheter 100. The catheter shaft 202 may be configured with a substantially circular cross-section, though other suitable configurations, such as elliptical, oval, or the like could be employed. Catheter shaft 202 may be flexible along its entire length or adapted for flexure along portions of its length to facilitate navigation through potentially torturous bodily vasculature.

Dimensions of catheter shaft 202 may be determined for a desired application. For example, catheter shaft 202 may generally be sized to fit within the catheter lumen 120 of support catheter 100, and the length of balloon catheter 200 may generally be greater than the length of the tubular portion 104 of support catheter 100. Any desired biocompatible material may be used to make the catheter shaft 202. In some embodiments, the catheter shaft 202 may be made of polymeric or metallic materials such as polyamide, PEBAX® (polyether block amide), polyurethane, polyethylene, nylon, polyethylene terepthalate, stainless steel or nitinol, or a combination of polymeric and metallic materials. Furthermore, the catheter shaft 202, or a portion thereof, may be made from polymers reinforced with metal wires, braids and/or coils, as known in the art.

The hub assembly 212 at the proximal end 204 may include components such as one or more ports such as ports 216 and 220. In general, ports 216, 220 may allow the insertion of various medical devices and/or substances into lumens extending within the body of the catheter. For example, ports 216, 220 may be used to introduce contrast media, inflation media, and/or guidewires, through the catheter shaft 202.

The balloon 214 may be an expandable element, as generally known in the art, mounted on a distal region of the catheter shaft 202 proximate to the distal end 206. In some instances, the balloon 214 may be positioned such that the distal end 206 protrudes only slightly, or not at all, beyond the balloon 214. In a deflated state, the balloon 214 may assume a generally cylindrical shape, with cross-sectional dimensions slightly greater than cross-sectional dimensions of the catheter shaft 202.

When inflated, however, the balloon 214 may be adapted to assume a variety of desired shapes, as might be most useful in a particular therapeutic situation. Known shapes include spherical, cylindrical, conical, elliptical, and similar configurations. Inflated shapes may be tailored to specific therapeutic scenarios, and in some embodiments, the inflated shape may be a few times greater than the cross-sectional dimensions of the catheter shaft 202. In some embodiments, the diameter of the inflated balloon 214 may be less than the cross-sectional dimensions of the vessel lumen where subintimal reentry is desired. The length of the balloon 214 may be similar or smaller than the length of an angioplasty balloon. In addition, the balloon 214 may be semi-pliable or non-pliable to exert a radially outward force on the layers of the vessel wall upon inflation.

Although the illustrated embodiments employ an inflatable balloon, it should be understood that any expandable element could be employed in other embodiments of the disclosure. For example, a self-expanding basket could be useful in some situations, particularly where expansion of a device is to be triggered solely by release of the device from the confines of a lumen rather than through the use of an inflation apparatus. These and other modifications will be clear to those of skill in the art. Further, the balloon 214 may be fabricated from one or more biocompatible material(s). Some exemplary suitable materials include polyamide, PEBA (polyether block amide), polyurethane, silicon, PET (polyethylene terepthalate), and other suitable polymers known in the art.

The balloon 214 may be operatively coupled to an inflation mechanism (not illustrated), such as a syringe, configured to provide pressurized fluid through the inflation lumen 210 to inflate the balloon 214 to an expanded configuration. The inflation mechanism may inject fluid in or draw fluid out in order to inflate or deflate the balloon 214, respectively.

In some embodiments, a penetration member 224 may be provided to penetrate through the intimal layer into the lumen of the blood vessel. For example, the penetration member 224 may be insertable through the guidewire lumen 208 or be mounted at the distal tip of balloon catheter 200. In some instances, the penetration member 224 may be formed as a sharp stylet, having a sharpened distal tip configured to project distally from the distal end 206 of the balloon catheter 200. As discussed below, the penetration member 224 may be designed to puncture the inner layer of the vessel wall to gain subintimal reentry into the true lumen of the vessel.

In some embodiments, as illustrated, the penetration member 224 may be a needle catheter. In such embodiments, the penetration member 224 may be inserted into the guidewire lumen 208 from port 216 to extend out of the distal opening 218 of the catheter shaft 202. The cross-sectional dimensions of the penetration member 224 may be smaller than the cross-sectional dimensions of the guidewire lumen 208, and the length of the penetration member 224 may be greater than the length of the balloon catheter 200.

In some other embodiments, the guidewire 118 (illustrated in FIGS. 1A-1C), or a separate guidewire, may be used as the penetration member 224. In such embodiments, after positioning the support catheter 100 within the vessel wall where subintimal reentry is desired, the guidewire 118 may be retracted from the support catheter 100 and inserted into the guidewire lumen 208 from port 216 to extend out of the distal opening 218 to penetrate the vessel wall. In other embodiments, a separate guidewire may be advanced through the guidewire lumen 208 to function as the penetration member 224 to penetrate the vessel wall.

In other embodiments, the penetration member 224 may be a flexible hypotube having a sharpened distal tip, and made of any suitable biocompatible material such as stainless steel or nitinol, for example. In such instances, the penetration member 224 may be slidably disposed within the guidewire lumen 208. In other instances, a penetration member 224 may be mounted to the distal end 206 of the catheter shaft 202 and extend therefrom.

In operation, the balloon catheter 200 may extend through the catheter lumen 120 and out of the distal opening 124 of the support catheter 100 such that the balloon 214 may align with the extension segment 110. The penetration member 224 may extend through the guidewire lumen 208 and extend out of the distal opening 218 of the balloon catheter 200.

Figure 3A:
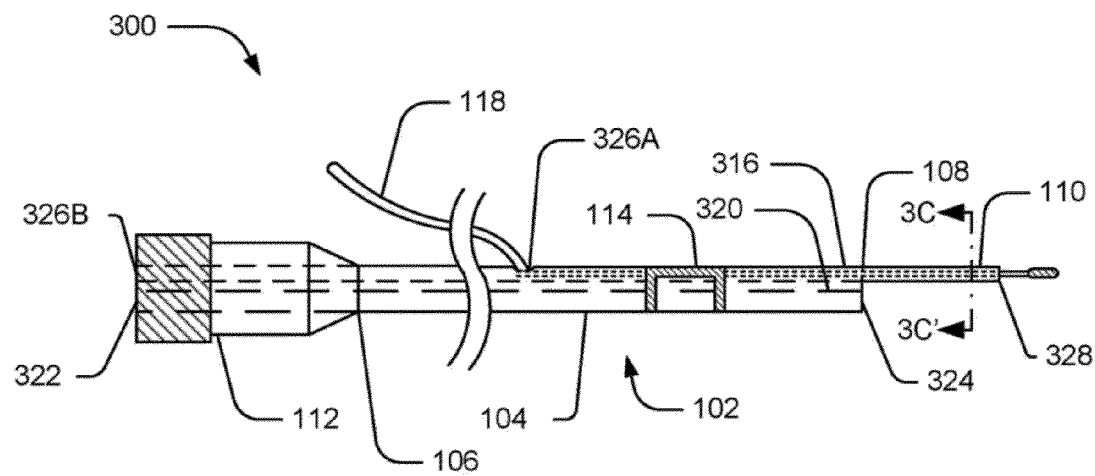
FIGS. 3A-3C illustrate another exemplary support catheter, where
Figure 3B:
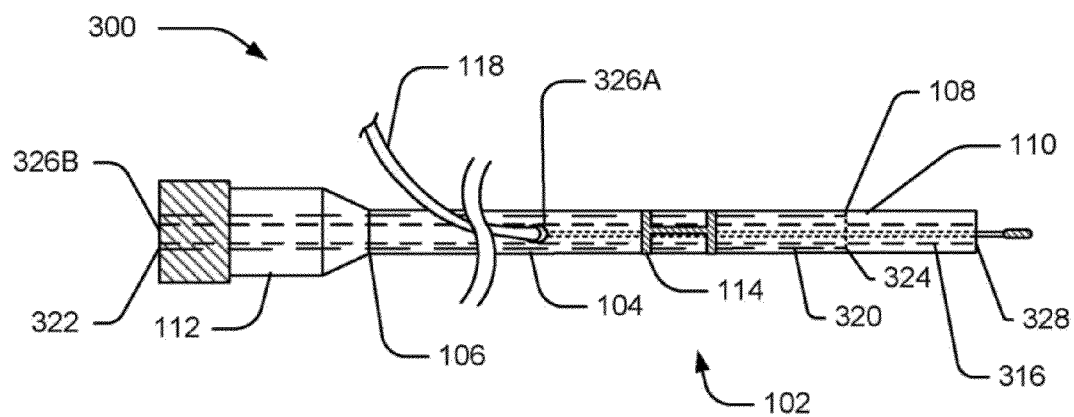
Figure 3C:
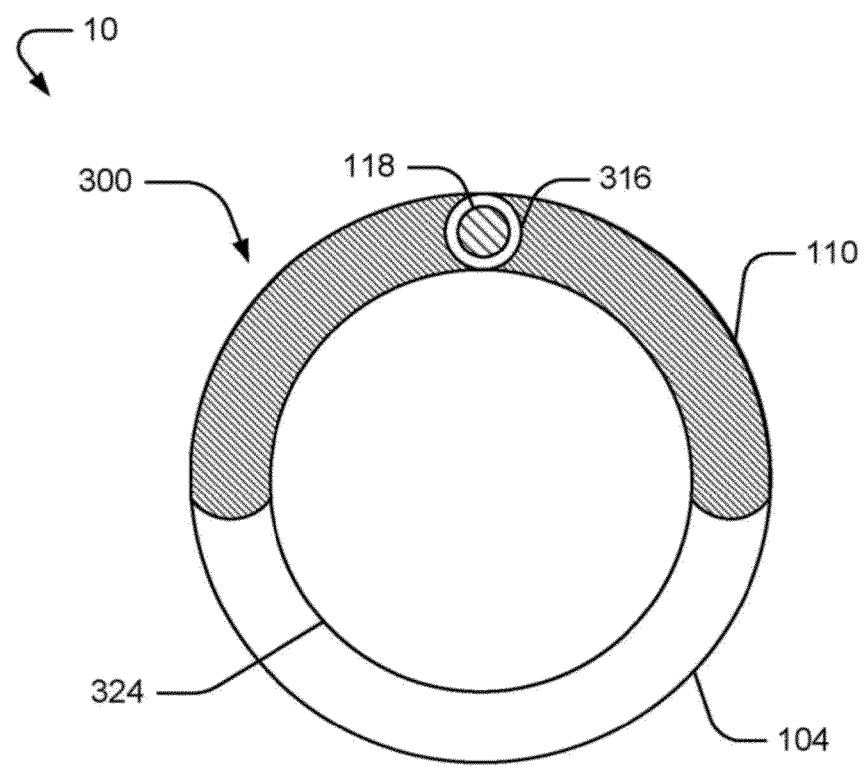

The recanalization catheter system 10, in some embodiments may include different embodiments of support catheter 100 and/or the balloon catheter 200. For example, another exemplary embodiment of the support catheter 300 is shown in FIGS. 3A-3C. FIGS. 3A and 3B are side and top views, respectively, and FIG. 3C is a cross-sectional view, taken along plane 3C-3C' of FIG. 3A. Support catheter 300 may be similar to the support catheter 100 of FIGS. 1A-1C, and may include the elongate shaft 102 (tubular portion 104, and extension segment 110), hub assembly 112, and marker band 114.

However, unlike support catheter 100 (shown in FIGS. 1A-1C), the support catheter 300 may include two lumens shown in FIGS. 3A-3B, namely, a guidewire lumen 316, and a balloon catheter lumen 320. The guidewire lumen 316 may be configured to receive the guidewire 118 therethrough and may extend from the hub assembly 112 to the distal end of the extension segment 110, in some instances. The balloon catheter lumen 320 may be configured to receive the balloon catheter 200 (FIG. 2) therethrough and may extend from the hub assembly 112 to the distal end 108 of the tubular portion 104, in some instances. The lumens 316 and 320 may communicate with one or more ports or openings in support catheter 300. For example, the proximal end of balloon catheter lumen 320 may terminate at port 322 and its distal end may terminate at a distal opening 324 located at, or near, the distal end 108 of the tubular portion 104.

The support catheter 300 may be configured to be advanced over the guidewire 118 for delivery to a remote location in the vasculature of a patient. In some embodiments, the support catheter 300 may be configured as a single operator exchange (SOE) (monorail or rapid exchange) catheter, having a rapid exchange port 326A located distal of the proximal end 106 of the tubular portion 104 for inserting the guidewire 118 into the guidewire lumen 316. In other embodiments, the support catheter 300 may be configured as an over the wire (OTW) catheter, having a port 326B configured at hub assembly 112 for inserting the guidewire 118 into the guidewire lumen 316. Furthermore, to extend the guidewire 118 distally from the support catheter 100, the distal end of the extension segment 110 may have a port 328 in communication with the guidewire lumen 316, thus extending the guidewire lumen 316 through the extension segment 110 to the distal end of the extension segment 110. It may be noted that in instances where the support catheter 100 is an SOE catheter, the hub assembly 112 may not include the port 326B. Where the support catheter 300 is an OTW catheter, however, the rapid exchange port 326A may be omitted. It is noted that other catheter constructions are contemplated.

FIG. 3C illustrates a cross-section of support catheter 300 across plane 3C-3C'. Here, extension segment 110, guidewire lumen 316, and the guidewire 118 are shown in cross-section, extending distally from tubular portion 104 beyond the distal opening 324. It can be seen that extension segment 110 may continue the upper portion of the profile of tubular portion 104 in the form of a closed semi-annulus, carrying the guidewire lumen 316 therethrough.

Lumens 316 and 320 may be configured to carry the guidewire 118 and the balloon catheter 200 (FIG. 2), respectively. The guidewire lumen 316 may have a diameter sized to accommodate the guidewire 118. For example, in some embodiments the diameter of the guidewire lumen 316 may be about 0.015 inches to about 0.036 inches. Similarly, the diameter of the balloon catheter lumen 320 may be sized to accommodate the balloon catheter 200. For example, in some embodiments, the diameter of the balloon catheter lumen 320 may be about 0.05 inches to about 0.10 inches.

Figure 4:
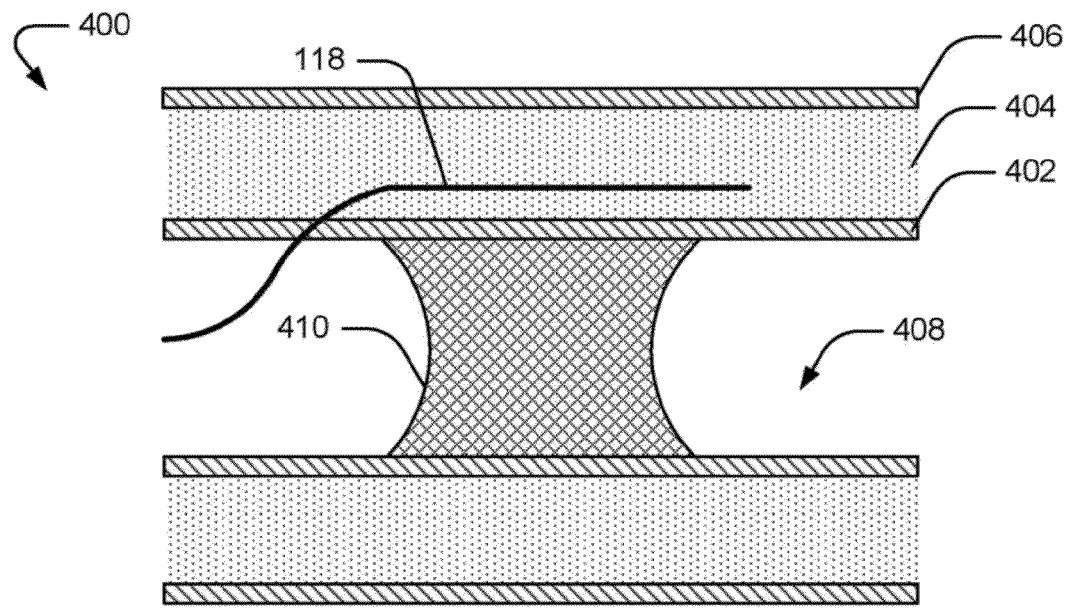
FIGS. 4-9 illustrate aspects of an exemplary method for reentering the true lumen of an occluded blood vessel using a subintimal recanalization catheter system as described herein.

FIGS. 4-9 illustrate aspects of an exemplary method for reentering the true lumen of an occluded blood vessel using the recanalization catheter system 10. As illustrated in FIG. 4, a blood vessel 400 has three tissue layers, an innermost or intimal layer 402 (tunica intima), an intermediate or media layer 404 (tunica media), and an outermost or adventitial layer 406 (tunica adventitia). Endothelial cells lining the lumen 408 of blood vessel 400, as well as a sub-endothelial layer of mostly loose connective tissue forms the intimal layer 402. The media layer 404 is formed primarily of circumferentially arranged smooth muscle cells. The adventitial layer 406 is made up of loose connective tissue including fibroblasts and associated collagen fibers.

In some instances, a chronic total occlusion (CTO) 410 may block the blood vessel 400 and may restrict or block blood flow though the vessel lumen 408. In some instances, a layer of plaque may accumulate on the intimal layer 402 distal of the occlusion 410. If possible, a physician may attempt to recanalize the vessel by pushing or cutting through the obstruction, but that procedure may not be successful. In such instances, it may be desirable to recanalize the vessel by going around the obstruction through a subintimal approach.

FIGS. 4-9 illustrate one possible subintimal approach utilizing the recanalization catheter system 10. As illustrated in FIG. 4, the guidewire 118 may initially be inserted into the vessel wall into the media layer 404 creating a subintimal space between the intimal and adventitial layers 402, 406. For example, the guidewire 118 may be advanced through the vessel lumen 408 to a location proximate the occlusion 410. The operator may then alter the direction of guidewire 118 so that the guidewire 118 penetrates outward through the intimal layer 402. With the tip of the guidewire 118 positioned between the intimal layer 402 and the adventitial layer 406, the guidewire 118 may be further moved distally between the intimal layer 402 and the adventitial layer 406. The guidewire 118 may be advanced until its distal tip lies distal of the distal end of the occlusion 410.

Figure 5:
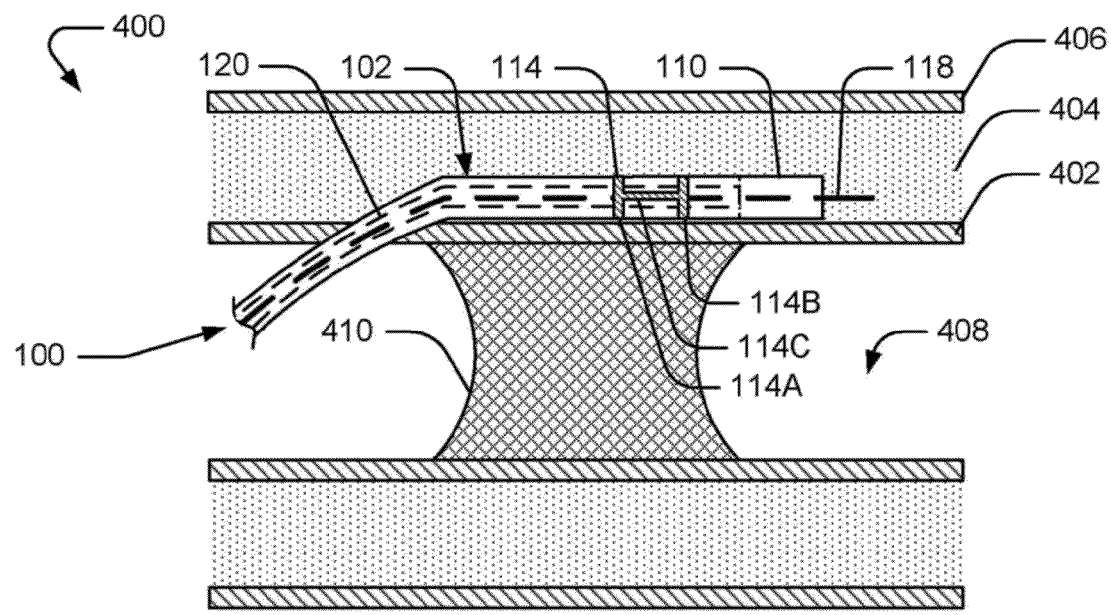

Then, as illustrated in FIG. 5, the elongate shaft 102 of the support catheter 100 may then be moved distally over the guidewire 118 (using catheter lumen 120) within the vessel lumen 408 while the hub assembly 112 may remain outside the patient's body. Further, the elongate shaft 102 may be moved forward from the vessel lumen 408, proximal of the occlusion 410 into the subintimal space between the intimal layer 402 and the adventitial layer 406, to a position in which the extension segment 110 is disposed distal of the distal end of the occlusion 410. Here it will be noted that movement and positioning of elongate shaft 102 may be facilitated by marker band 114 that allows the operator to accurately track the positioning and rotational orientation of elongate shaft 102 as it travels around the occlusion 410 in the vessel wall.

Figure 6:
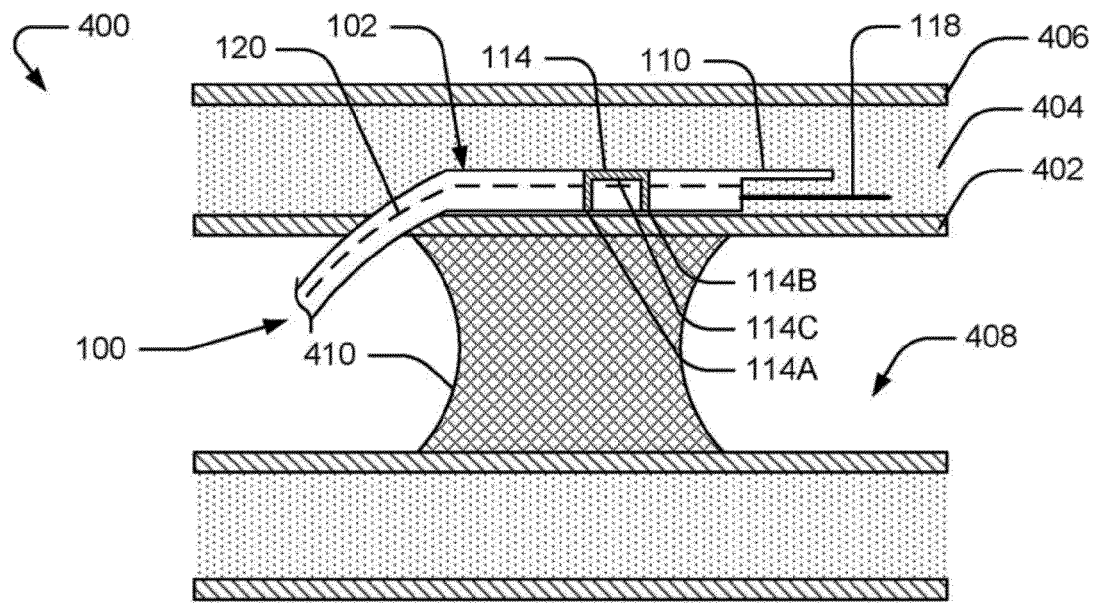

FIG. 6 depicts reorientation of the elongate shaft 102 within the subintimal space. After the distal tip of elongate shaft 102 approaches the desired position, the operator may use appropriate imaging means, such as fluoroscopy, to visualize the marker band 114. The resulting image may show the forward progress of elongate shaft 102, as well as the rotational orientation of elongate shaft 102. In the illustrated example, marker band 114 includes two circumferential rings 114A and 114B joined by a longitudinal bar 114C, with the bar 114C aligned with extension segment 110. Thus, viewing the marker band 114 may allow the operator to manipulate the elongate shaft 102 so that the extension segment 110 may be located at a dorsal position with respect to intimal layer 402. In other words, the marker band 114 may assist the operator in rotationally orienting the elongate shaft 102 such that the convex side of the extension segment 110 is positioned toward the adventitial layer 406, and thus away from the true lumen 408, and the concave side of the extension segment 110 is positioned toward the intimal layer 402, and thus the true lumen 408.

Comparison of FIG. 5 with FIG. 6 illustrates this process of rotationally orienting the elongate shaft 102. In FIG. 5, visualization of elongate shaft 102 shows that the bar 114C on marker band 114 is located toward intimal layer 402, indicating that extension segment 110 is similarly rotated toward intimal layer 402. Thus, the operator may rotate elongate shaft 102 so that the elongate shaft 102 achieves the rotational position shown in FIG. 6, which reveals that the bar 114C, and thus extension segment 110, is positioned completely dorsal to the intimal layer 402. In other words, the operator may rotate the elongate shaft 102 until the bar 114C is located at a rotational position furthest away from the lumen 408, thus indicating the extension segment 110 is similarly positioned at a rotational position furthest way from the lumen 408. In such an orientation, the extension segment 110 may be positioned between the balloon 214 and the adventitial layer 406.

Figure 7:
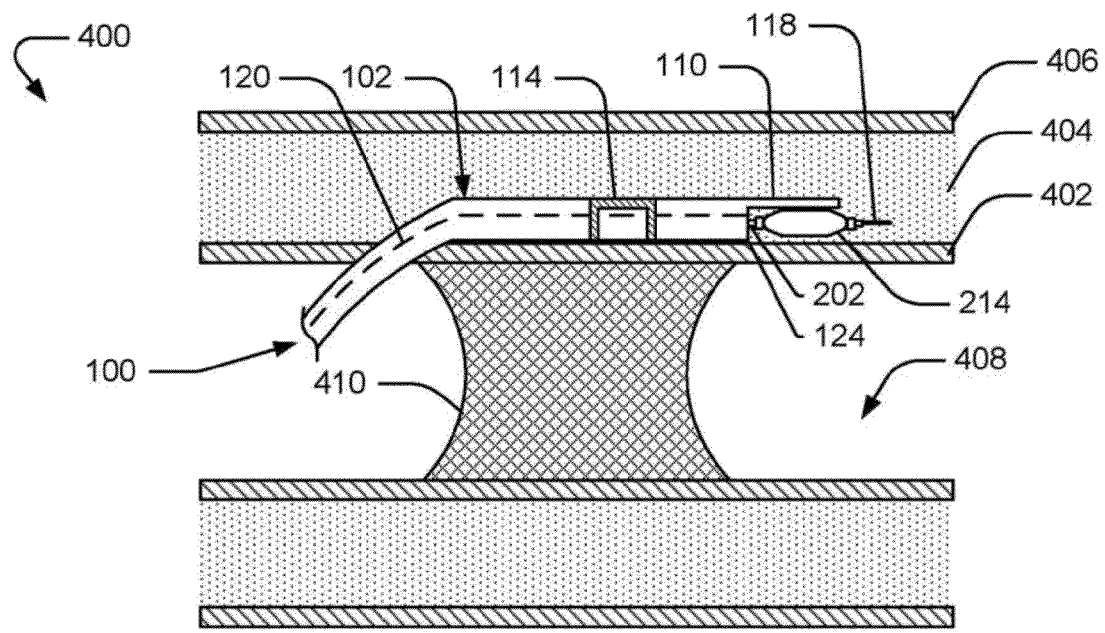

After reorienting the elongate shaft 102, shown in FIG. 7, the operator may retract the guidewire 118 and advance the balloon catheter 200 (with the balloon 214 in a deflated configuration) outward from the catheter lumen 120 such that a distal portion of the catheter shaft 202 including the balloon 214 may extend out of the distal opening 124 and along the extension segment 110. In addition, the balloon 214 may lie parallel to the extension segment 110 without extending beyond the extension segment 110. Thus, the balloon 214 may be positioned beside the extension segment 110, with the extension segment 110 located radially outward of the balloon 214 (further from the lumen 408 than the balloon 214).

Figure 8:
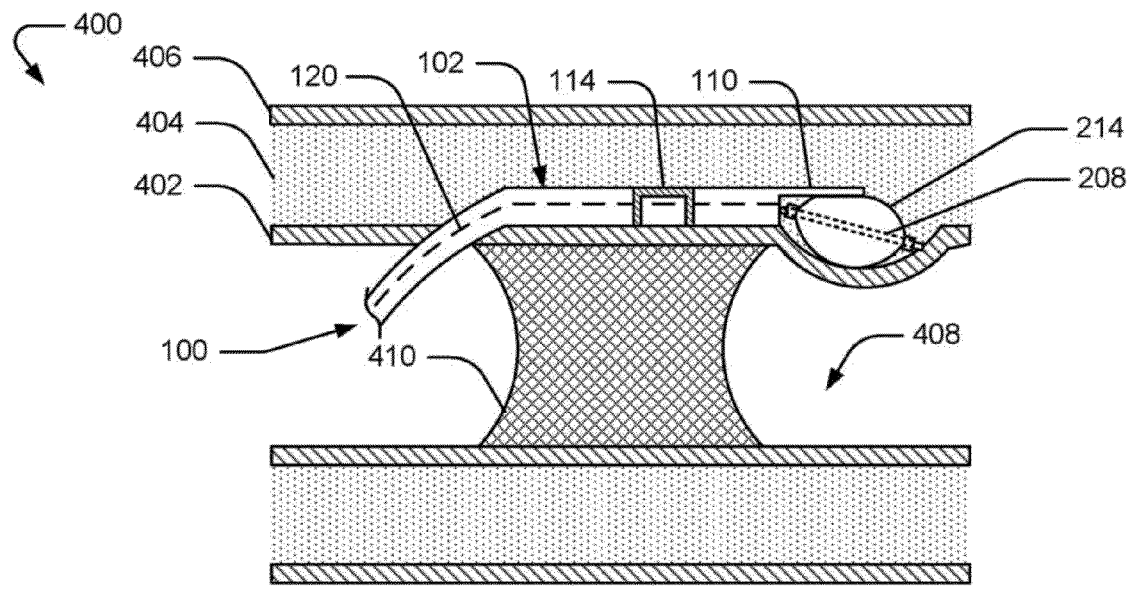

FIG. 8 illustrates an exemplary expansion of the balloon 214. With balloon 214 in position between the extension segment 110 and the intimal layer 402, as described above, the operator may inflate the balloon 214 with a suitable inflation media. Inflation of the balloon 214 may exert a force in a radially outward direction. Because inflation begins with balloon 214 generally aligned with and juxtaposed with extension segment 110, some radial force is exerted against extension segment 110. The extension segment 110, positioned between the balloon 214 and the adventitial layer 406 enhances the ability of the balloon 214 to bend or deflect the distal portion of the balloon catheter 200 toward the lumen 408. For instance, the stiffness of the extension segment 110 may be combined with the stiffness of the adventitial layer 406. The combined stiffness of the extension segment 110 and adventitial layer 406, thus will be greater than the stiffness of the adventitial layer 406 alone, and generally exceed the stiffness of the intimal layer 402. Accordingly, when the balloon 214 is inflated, the intimal layer 402 may bulge or yield inwardly into the lumen 408 as the balloon 214 presses against the extension segment 110, which doesn't yield or yields considerably less. The lack of movement in a radially outward direction coupled with the considerable deflection radially inward causes the distal portion of the catheter shaft 202 extending through the balloon 214 to deflect or rotate radially inward toward the vessel lumen 408.

Figure 9:
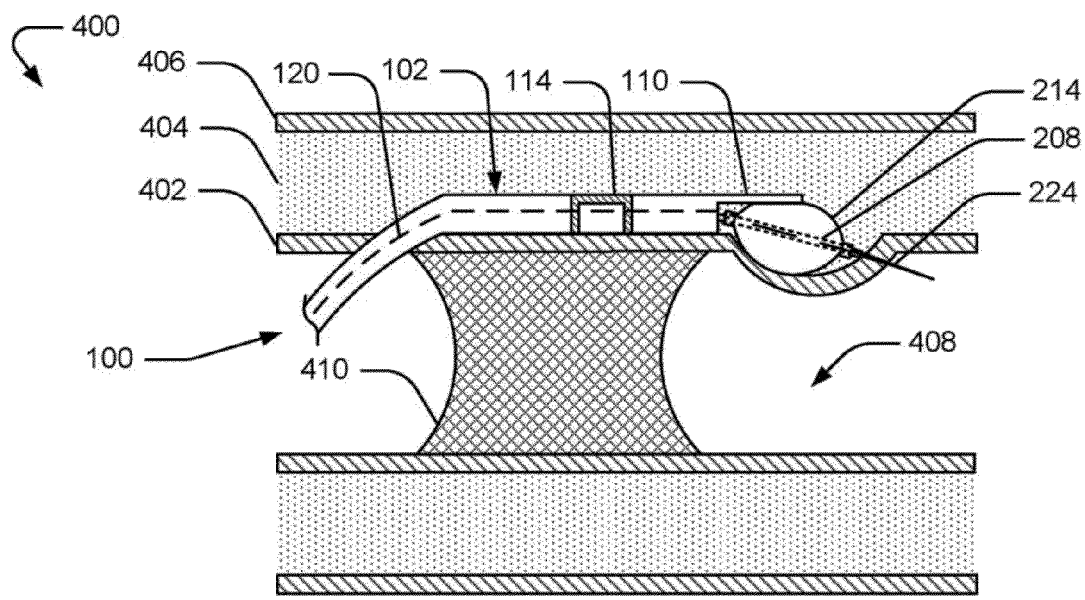

FIG. 9 depicts the penetration member 224 penetrating through the intimal layer 402 back into the true lumen 408. After inflating the balloon 214 to deflect the distal portion of the catheter shaft 202 toward the true lumen 408, the operator may distally extend the penetration member 224 out of the distal tip of the catheter shaft 202. Because the axis of the guidewire lumen 208 points downward toward the vessel lumen 408, application of suitable force may press the penetration member 224 into and through the intimal layer 402, thereby reentering the vessel lumen 408 distal of the occlusion 410.

Penetration through the intimal layer 402 may create a reentry path out of vessel lumen 408 proximal of the occlusion 410, through the subintimal space, and back into vessel lumen 408 distal of the occlusion 410. The penetration member 224 may be withdrawn and replaced with a guidewire. Thereafter, the support catheter 100 and the balloon catheter 200 may be withdrawn and one or more additional medical devices may be advanced through the blood vessel 400 to enlarge the pathway and/or pass distally of the occlusion 410 to perform a further medical procedure.

Figure 10:
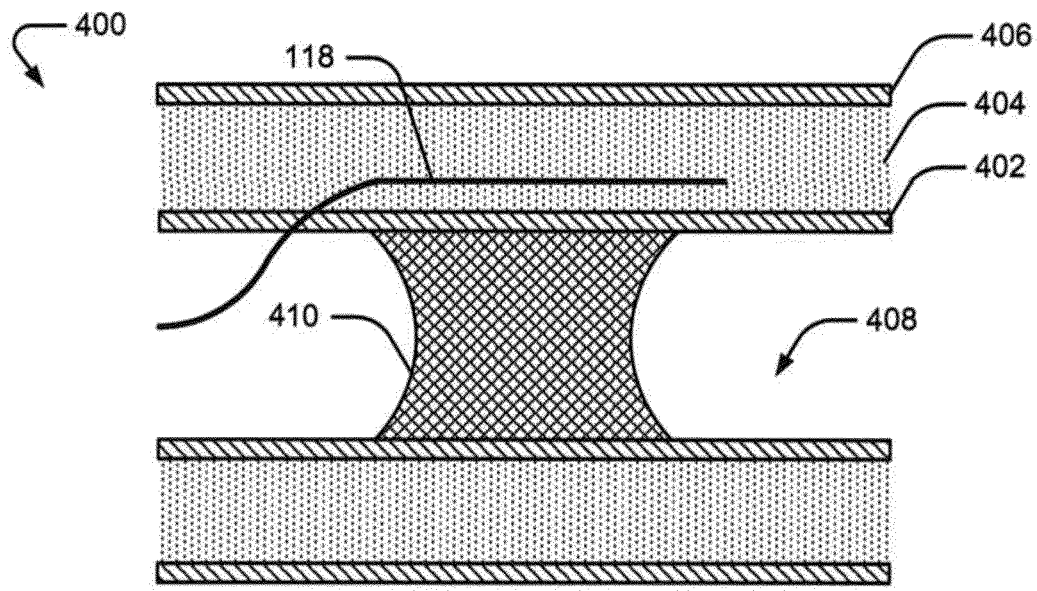
FIGS. 10-15 illustrate aspects of an exemplary method for reentering the true lumen of an occluded blood vessel using a subintimal recanalization catheter system having the support catheter described in FIGS. 3A-3C.
Figure 11:
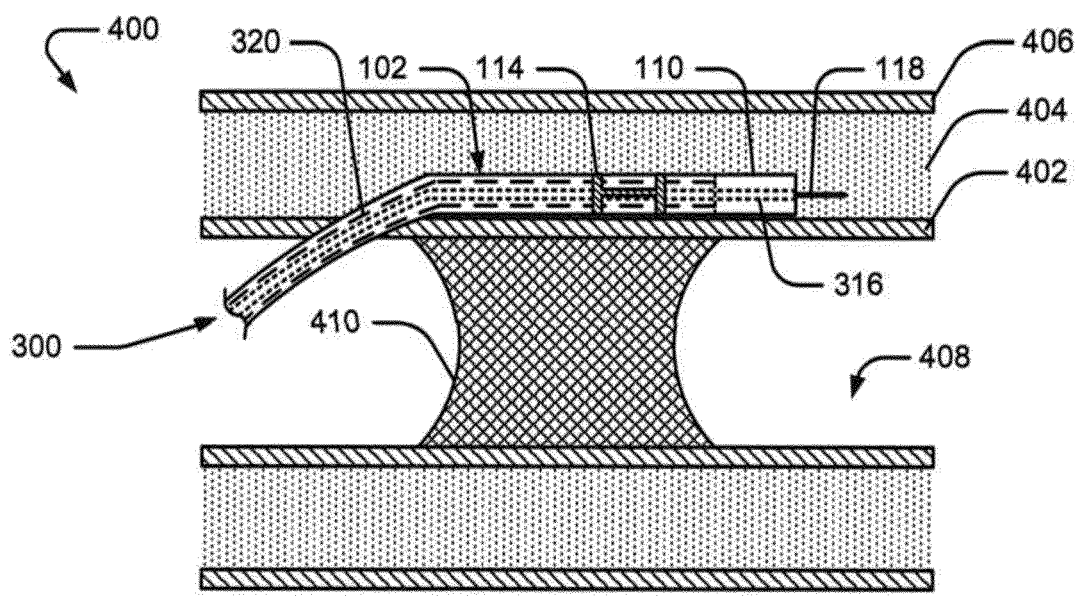
Figure 12:
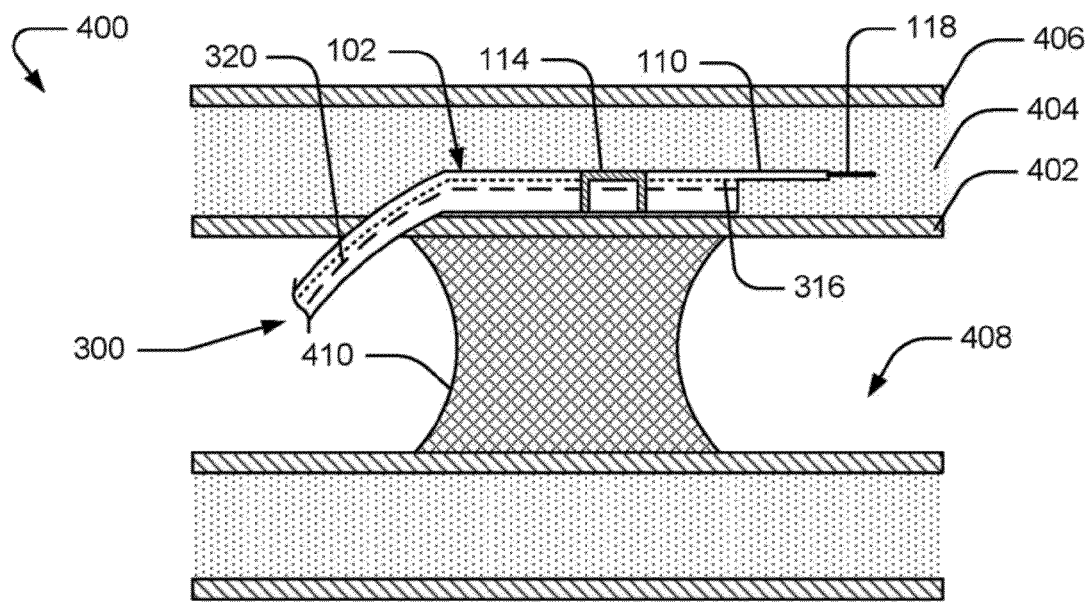
Figure 13:
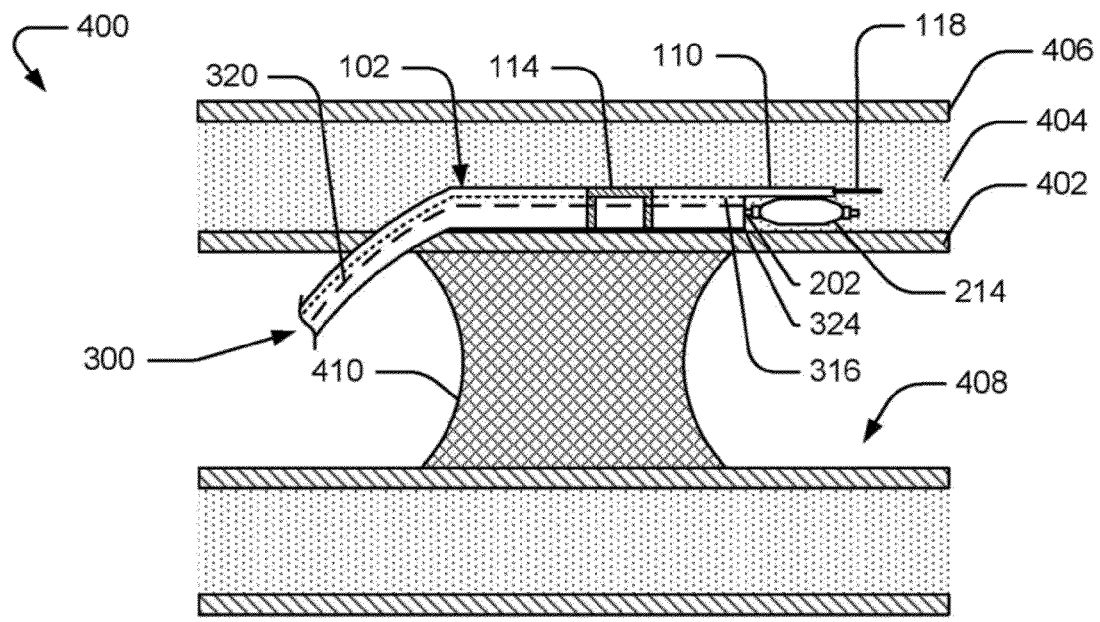

FIGS. 10-15 illustrate another possible subintimal approach utilizing the recanalization catheter system 10 having support catheter 300. Similar to the subintimal approach discussed in FIGS. 4-9, the approach is illustrated with the exemplary blood vessel 400. As shown in FIG. 10, similar to FIG. 4, the guidewire 118 may initially be inserted into the vessel wall into the media layer 404 creating a subintimal space between the intimal and adventitial layers 402, 406. Then, as illustrated in FIG. 11, similar to FIG. 5, the elongate shaft 102 of the support catheter 300 may then be moved distally over the guidewire 118 (using guidewire lumen 316) within the vessel lumen 408 while the hub assembly 112 may remain outside the patient's body. Further, the elongate shaft 102 may be moved forward from proximal of the occlusion 410 to distal of the occlusion 410. As discussed, the movement and positioning of elongate shaft 102 may be facilitated by marker band 114. Similar to FIG. 6, FIG. 12 depicts reorientation of the elongate shaft 102 within the subintimal space. After the distal tip of elongate shaft 102 approaches the desired position, the operator may use appropriate imaging means, such as fluoroscopy, to visualize the marker band 114 and manipulate the position and orientation of the elongate shaft 102 such that the elongate shaft 102 is positioned at the desired location and the extension segment 110 may be positioned between the balloon 214 and the adventitial layer 406. After reorienting the elongate shaft 102, shown in FIG. 13, similar to FIG. 7, the operator may advance the balloon catheter 200 (with the balloon 214 in a deflated configuration) outward from the balloon catheter lumen 320 such that a distal portion of the catheter shaft 202 including the balloon 214 may extend out of the distal opening 324 and along the extension segment 110. In addition, the balloon 214 may lie parallel to the extension segment 110 without extending beyond the extension segment 110. Thus, the balloon 214 may be positioned beside the extension segment 110, with the extension segment 110 located radially outward of the balloon 214 (further from the lumen 408 than the balloon 214).

Figure 14:
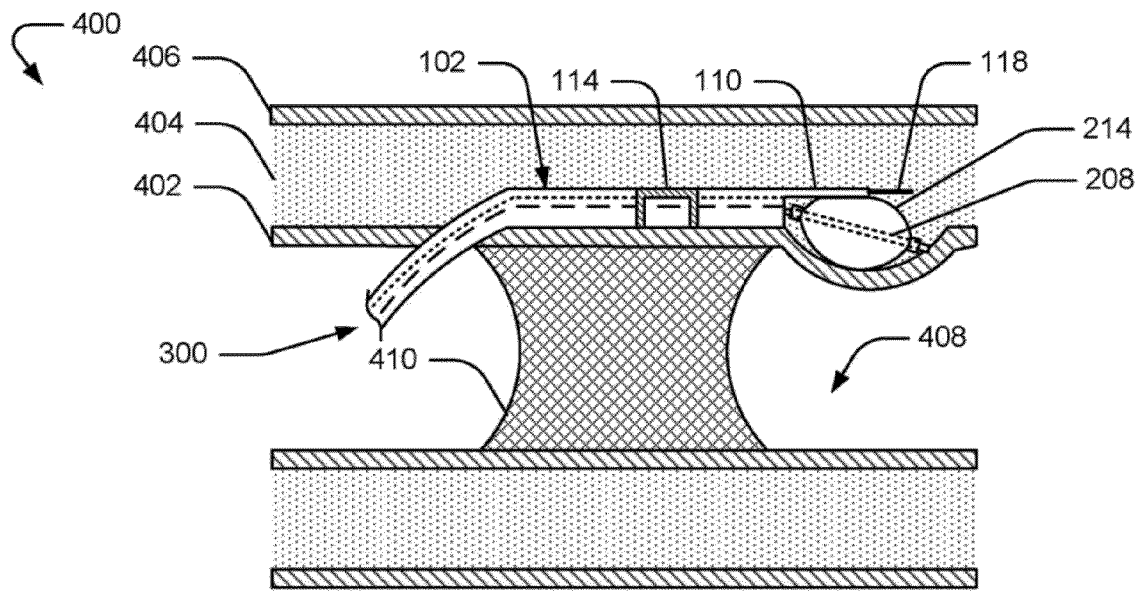
Figure 15:
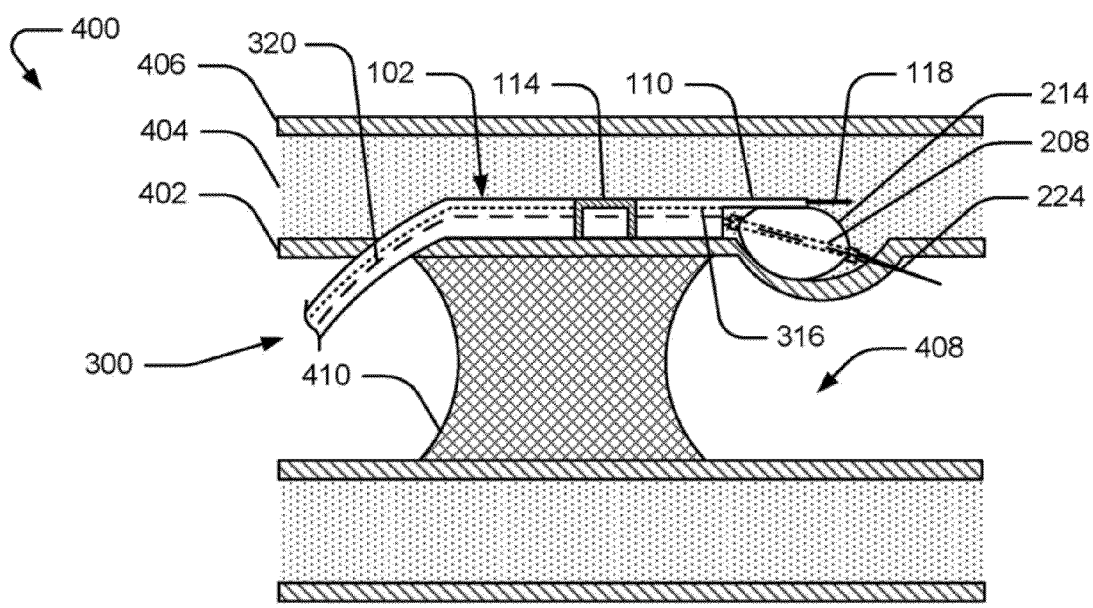

Then, as shown in FIG. 14, similar to FIG. 8, the operator may inflate the balloon 214 to exert a force in a radially outward direction. The balloon 214 inflation may allow the intimal layer 402 to bulge or yield inwardly into the lumen 408, while the extension segment 110 may not yield because of its higher stiffness. The lack of movement in a radially outward direction coupled with the considerable deflection radially inward causes the distal portion of the catheter shaft 202 extending through the balloon 214 to deflect or rotate radially inward toward the vessel lumen 408. After radially inward deflection of the distal portion of the catheter shaft 202, as shown in FIG. 15, similar to FIG. 9, the operator may distally extend the penetration member 224 out of the distal tip of the catheter shaft 202. As the axis of the guidewire lumen 208 points downward toward the vessel lumen 408, application of suitable force may press the penetration member 224 into and through the intimal layer 402, thereby reentering the vessel lumen 408 distal of the occlusion 410 and creating a reentry path to perform further medical procedures.

Figure 16:
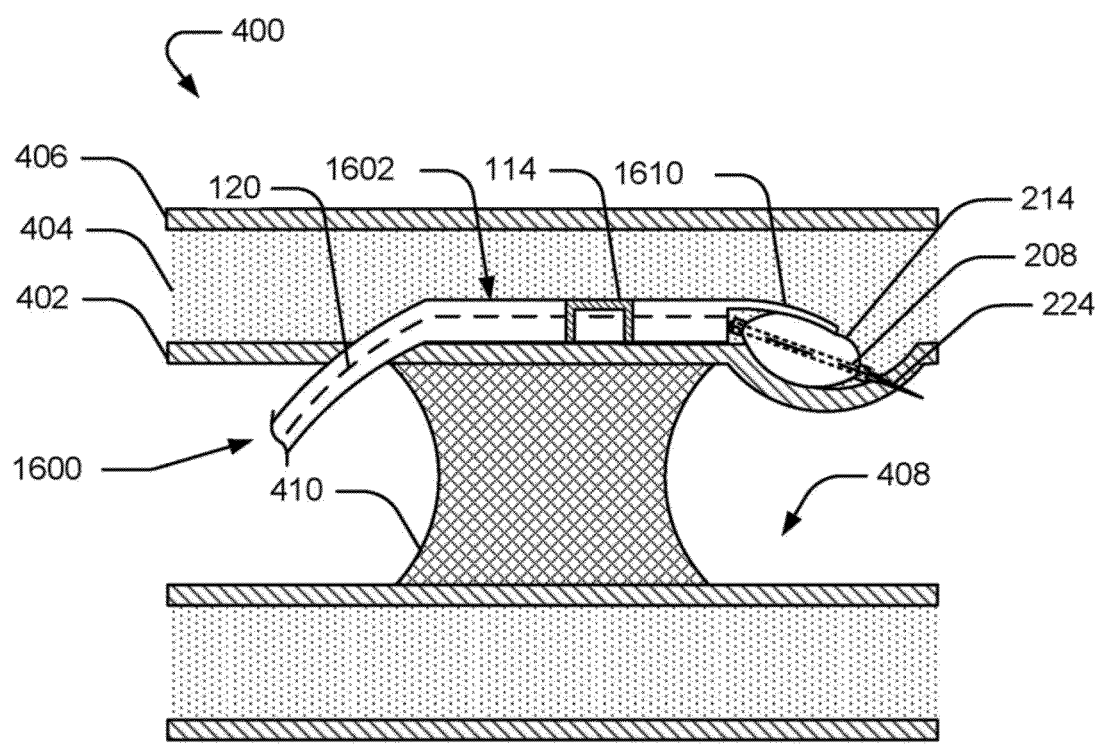
FIG. 16 illustrates an alternative exemplary embodiment of a support catheter for reentering the true lumen of an occluded blood vessel.

FIG. 16 illustrates an alternative exemplary embodiment of a support catheter 1600 for reentering the true lumen of the occluded blood vessel 400, which in many respects may be similar to the support catheter 100. For example, the support catheter 1600 may include an elongate shaft 1602 having an extension segment 1610 extending distally of a distal opening of a tubular portion of the elongate shaft 1602. As illustrated, the extension segment 1610 may have a bent or curved structure with the distal end of the extension segment 1610 located closer to the central longitudinal axis of the elongate shaft 1602 than the proximal end of the extension segment 1610. The curved or bent configuration of the extension segment 1610 may be provided such that after positioning and rotationally orienting the elongate shaft 1602 at the desired location (distal of the distal end of the occlusion 410) within the subintimal space, the distal end of the extension segment 1610 may lie at a ventral location with respect to the proximal end of the extension segment 1610. In other words, the distal end of the extension segment 1610 may be located closer to the vessel lumen 408 than the proximal end of the extension segment 1610. This bent or curved structure may facilitate in orienting the balloon 214 and the distal portion of the catheter shaft 202 extending through the balloon 214 towards the vessel lumen 408.

Figure 17A:
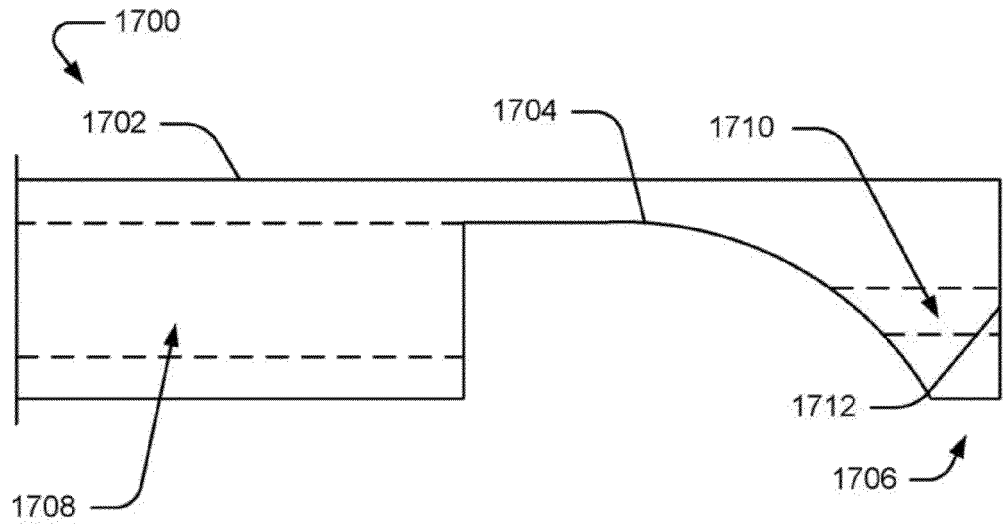
FIGS. 17A-17B depict another alternative exemplary embodiment of a support catheter for reentering the true lumen of an occluded blood vessel.
Figure 17B:
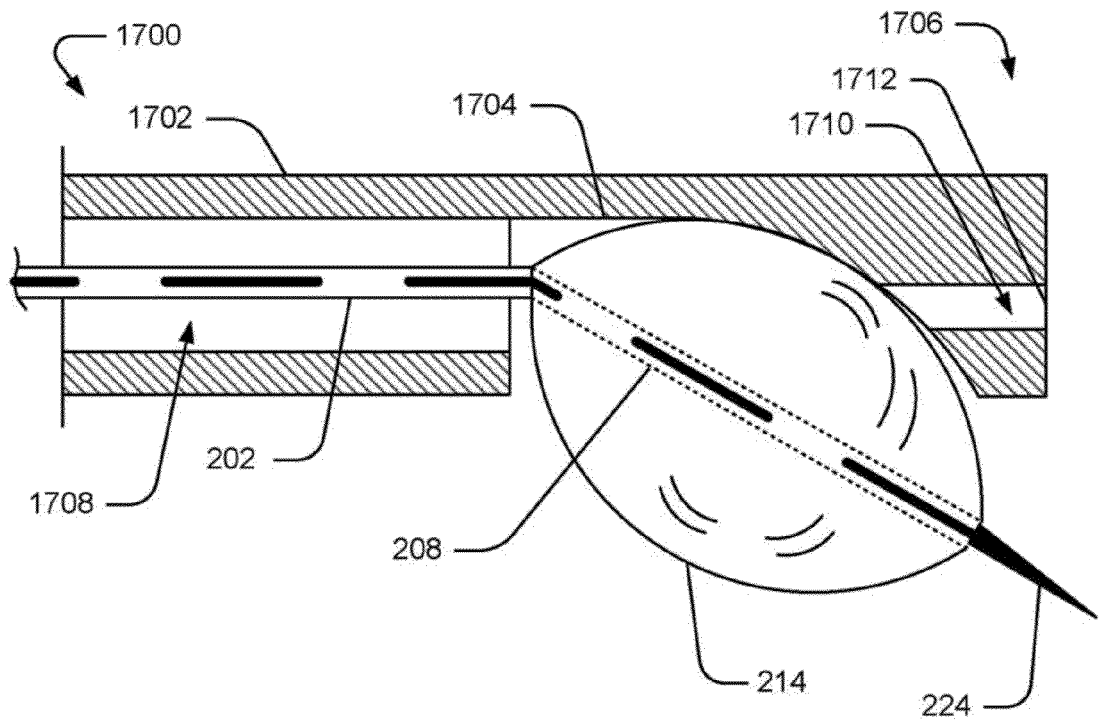

FIGS. 17A-17B depict another alternative exemplary embodiment of a support catheter 1700 for reentering the true lumen of an occluded blood vessel. FIG. 17A depicts a distal portion of an elongate shaft 1702, and FIG. 17B exhibits the balloon catheter 200 within the elongate shaft 1702. As illustrated in FIG. 17A, the distal portion of elongate shaft 1702 may include an opening 1704 proximate to the distal end 1706 such the elongate shaft 1702 extends distally beyond the opening 1704. The opening 1704 may communicate with the lumens 1708 and 1710. The lumen 1708 may be adapted to receive the balloon catheter 200 therethrough, and the lumen 1710 may be adapted to receive the guidewire 118 therethrough. The guidewire 118 (not illustrated) may pass through the lumen 1710 to extend out of a distal opening 1712 to guide the catheter 1700 within a patient's vasculature. After insertion of the balloon catheter 200 (not illustrated) within lumen 1708 with the balloon 214 in a deflated configuration, the guidewire 118 (not illustrated) may be withdrawn proximal into the guidewire lumen 208 of the balloon catheter 200 proximal of the lumen 1710.

As seen in FIG. 17B, the opening 1704 may function as an extension segment (illustrated in FIGS. 1A-1C) for inflating the balloon 214 thereagainst. The distal portion of the opening 1704 may be configured with a slope to facilitate deflection of the balloon catheter 200 out of the elongate shaft 1702. Similar to the method described with FIGS. 4-9, for subintimal reentry, the opening 1704 may be positioned within a subintimal space distal of the distal end of an occlusion (not illustrated) such that the opening 1704 may face the intimal layer (not illustrated). As illustrated, as the balloon 214 may be inflated within the opening 1704 the distal portion of the catheter shaft 202 extending through the balloon 214 may deflect towards the vessel lumen. This outward deflection of the balloon 214 and the catheter shaft 202 may orient the distal opening 218 in communication with guidewire lumen 208 towards the intimal layer (not illustrated). The penetration member 224 may then penetrate the intimal layer through the distal opening 218, thereby creating a reentry path to the vessel lumen (not illustrated) distal of the occlusion (not illustrated).

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A subintimal recanalization catheter system for recanalizing a blood vessel having an occlusion in a lumen thereof, the catheter system comprising:
    an elongate shaft including a tubular portion having a lumen extending therethrough to a distal opening and an extension segment extending distal of the distal opening; and
    a balloon catheter having a balloon secured to a distal portion of a catheter shaft, the balloon catheter extendable through the lumen of the elongate shaft to position the balloon of the balloon catheter distal of the distal opening;
    wherein the catheter system is configured to be advanced into a subintimal space between a first tissue layer and a second tissue layer of a wall of the blood vessel; and
    wherein the balloon is configured to be inflated against the extension segment to cause the distal portion of the catheter shaft to deflect toward the lumen of the blood vessel within the subintimal space to facilitate reentry into the lumen of the blood vessel.

2. The subintimal recanalization catheter system of claim 1, wherein the extension segment has a stiffness greater than a stiffness of the first tissue layer.

3. The subintimal recanalization catheter system of claim 2, wherein the stiffness of the extension segment is additive to a stiffness of the second tissue layer to preferentially cause the first tissue layer to yield before the second tissue layer yields to inflation of the balloon.

4. The subintimal recanalization catheter system of claim 1, wherein the extension segment includes a guidewire lumen for receiving a guidewire therethrough.

5. The subintimal recanalization catheter system of claim 4, wherein the guidewire lumen extends into the tubular portion of the elongate shaft.

6. The subintimal recanalization catheter system of claim 1, further comprising: a penetration member extendable through the catheter shaft to penetrate through the first tissue layer into the lumen of the blood vessel distal of the occlusion.

7. The subintimal recanalization catheter system of claim 6, wherein the penetration member is extendable from a distal opening of the catheter shaft distal of the balloon.

8. The subintimal recanalization catheter system of claim 1, wherein the balloon is positionable alongside the extension segment prior to inflating the balloon.

9. The subintimal recanalization catheter system of claim 8, wherein the extension segment includes a concave surface facing the balloon.

10. A subintimal recanalization catheter system for recanalizing a blood vessel having an occlusion in a lumen thereof, the catheter system comprising:
    a support catheter including an elongate shaft including a tubular portion having a lumen extending therethrough to a distal opening and an extension segment extending distal of the distal opening; and
    a balloon catheter having a balloon secured to a distal portion of a catheter shaft, the balloon catheter extendable through the lumen of the elongate shaft to position the balloon of the balloon catheter alongside the extension segment distal of the distal opening;
    wherein the catheter system is configured to be advanced into a subintimal space between a first tissue layer and a second tissue layer of a wall of the blood vessel; and
    wherein the balloon is configured to be inflated between the extension segment and the first tissue layer;
    wherein the extension segment is positionable between the second tissue layer and the balloon; and
    wherein the balloon is inflatable against the extension segment to cause the distal portion of the catheter shaft to deflect toward the lumen of the blood vessel within the subintimal space to facilitate reentry into the lumen of the blood vessel.

11. The subintimal recanalization catheter system of claim 10, wherein a stiffness of the extension segment is additive to a stiffness of the second tissue layer to preferentially cause the first tissue layer to yield before the second tissue layer yields to cause the distal portion of the catheter shaft to deflect toward the lumen of the blood vessel within the subintimal space.

12. The subintimal recanalization catheter system of claim 11, further comprising:
    a penetration member extendable through the catheter shaft to penetrate through the first tissue layer into the lumen of the blood vessel distal of the occlusion.

13. The subintimal recanalization catheter system of claim 12, wherein the penetration member is extendable from a distal opening of the catheter shaft distal of the balloon.

* * * * *